US010359520B2

(12) United States Patent
Ishii et al.

(10) Patent No.: US 10,359,520 B2
(45) Date of Patent: Jul. 23, 2019

(54) RADIATION IMAGING SYSTEM, SIGNAL PROCESSING APPARATUS, AND SIGNAL PROCESSING METHOD FOR RADIOGRAPHIC IMAGE

(71) Applicant: CANON KABUSHIKI KAISHA, Tokyo (JP)

(72) Inventors: Yoshiaki Ishii, Kawasaki (JP); Atsushi Iwashita, Tokyo (JP); Sho Sato, Tokyo (JP); Kosuke Terui, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 15/980,040

(22) Filed: May 15, 2018

(65) Prior Publication Data

US 2018/0267177 A1    Sep. 20, 2018

Related U.S. Application Data

(63) Continuation of application No. PCT/JP2016/004707, filed on Oct. 26, 2016.

(30) Foreign Application Priority Data

Nov. 20, 2015    (JP) ................... 2015-228012

(51) Int. Cl.
*A61B 6/00* (2006.01)
*G01N 23/04* (2018.01)
*G01T 1/208* (2006.01)

(52) U.S. Cl.
CPC ............ *G01T 1/208* (2013.01); *A61B 6/4208* (2013.01); *A61B 6/4241* (2013.01);
(Continued)

(58) Field of Classification Search
CPC .............................. G01T 1/208; A61B 6/4208
See application file for complete search history.

(56) References Cited

U.S. PATENT DOCUMENTS

| 4,651,005 A * | 3/1987 | Baba .................. A61B 6/032 |
|---|---|---|
| | | 250/360.1 |
| 6,281,504 B1 * | 8/2001 | Takayama ............ G01T 1/1615 |
| | | 250/363.04 |

(Continued)

FOREIGN PATENT DOCUMENTS

| JP | 63-171387 A | | 7/1988 |
|---|---|---|---|
| JP | 63171387 A | * | 7/1988 |
| JP | 2002-90318 A | | 3/2002 |

OTHER PUBLICATIONS

International Search Report and Written Opinion of the International Searching Authority, dated Nov. 29, 2016.

*Primary Examiner* — David P Porta
*Assistant Examiner* — Djura Malevic
(74) *Attorney, Agent, or Firm* — Canon U.S.A., Inc. IP Division

(57) ABSTRACT

An energy resolution decrease in a radiation imaging apparatus is suppressed. The apparatus includes a detector including a conversion unit configured to convert incident radiation photons into optical photons or charges, a pixel array including pixels arranged in a two-dimensional matrix and configured to obtain a pixel value in accordance with the optical photons or charges, and an output circuit including a plurality of output channels configured to output the pixel value from the pixel array, and a signal processing unit configured to perform signal processing of correcting the pixel value by using a correction coefficient in accordance with a pixel value obtaining process model in which a process of obtaining the pixel value output from the pixel array via the plurality of output channels on the basis of the optical photons or charges is modeled and obtaining an energy-discriminated radiographic image based on the corrected pixel value.

12 Claims, 11 Drawing Sheets

(52) U.S. Cl.
CPC ............ *A61B 6/5258* (2013.01); *G01N 23/04* (2013.01); *G01N 2223/423* (2013.01)

(56) References Cited

U.S. PATENT DOCUMENTS

| | | | | |
|---|---|---|---|---|
| 6,714,621 | B2* | 3/2004 | Rick | A61B 6/481 |
| | | | | 378/18 |
| 7,496,176 | B2* | 2/2009 | Aslund | A61B 6/502 |
| | | | | 378/37 |
| 7,595,492 | B2* | 9/2009 | Nakamura | C09K 11/7774 |
| | | | | 250/361 R |
| 7,696,483 | B2* | 4/2010 | Tkaczyk | G01T 1/171 |
| | | | | 250/370.06 |
| 8,213,566 | B2* | 7/2012 | Roessl | A61B 5/4869 |
| | | | | 378/5 |
| 8,492,728 | B2* | 7/2013 | Antonuk | H01L 27/1462 |
| | | | | 250/370.11 |
| 8,637,832 | B2* | 1/2014 | Watanabe | G01T 1/247 |
| | | | | 250/394 |
| 8,754,379 | B2* | 6/2014 | Antonuk | H01L 27/1462 |
| | | | | 250/370.11 |
| 9,213,108 | B2* | 12/2015 | Nagai | A61B 6/4233 |
| 9,395,453 | B2* | 7/2016 | Antonuk | H01L 27/1462 |
| 9,568,618 | B2* | 2/2017 | Nishihara | H04N 5/32 |
| 9,841,389 | B2* | 12/2017 | Tamura | G01N 23/046 |
| 9,880,296 | B2* | 1/2018 | Antonuk | H01L 27/1462 |
| 10,024,979 | B1* | 7/2018 | Viswanath | G01T 1/17 |
| 2008/0099689 | A1* | 5/2008 | Nygard | G01T 1/2018 |
| | | | | 250/370.09 |
| 2008/0260094 | A1* | 10/2008 | Carmi | A61B 6/032 |
| | | | | 378/19 |
| 2010/0025593 | A1* | 2/2010 | Proksa | G01T 1/2928 |
| | | | | 250/370.09 |
| 2010/0232568 | A1* | 9/2010 | Heismann | G01T 1/24 |
| | | | | 378/19 |
| 2010/0320391 | A1* | 12/2010 | Antonuk | H01L 27/1462 |
| | | | | 250/366 |
| 2011/0012014 | A1* | 1/2011 | Livne | A61B 6/032 |
| | | | | 250/252.1 |
| 2012/0305791 | A1* | 12/2012 | Watanabe | G01T 1/247 |
| | | | | 250/394 |
| 2013/0292573 | A1* | 11/2013 | Antonuk | H01L 27/1462 |
| | | | | 250/361 R |
| 2014/0105370 | A1* | 4/2014 | Yamakawa | A61B 6/025 |
| | | | | 378/207 |
| 2014/0246596 | A1* | 9/2014 | Antonuk | H01L 27/1462 |
| | | | | 250/369 |
| 2014/0328466 | A1* | 11/2014 | Proksa | G06F 7/64 |
| | | | | 378/62 |
| 2015/0115163 | A1* | 4/2015 | Nishihara | H04N 5/32 |
| | | | | 250/366 |
| 2015/0198725 | A1* | 7/2015 | Tamura | G01N 23/046 |
| | | | | 378/5 |
| 2015/0301195 | A1* | 10/2015 | Antonuk | H01L 27/1462 |
| | | | | 250/369 |
| 2017/0045629 | A1* | 2/2017 | Antonuk | H01L 27/1462 |

\* cited by examiner

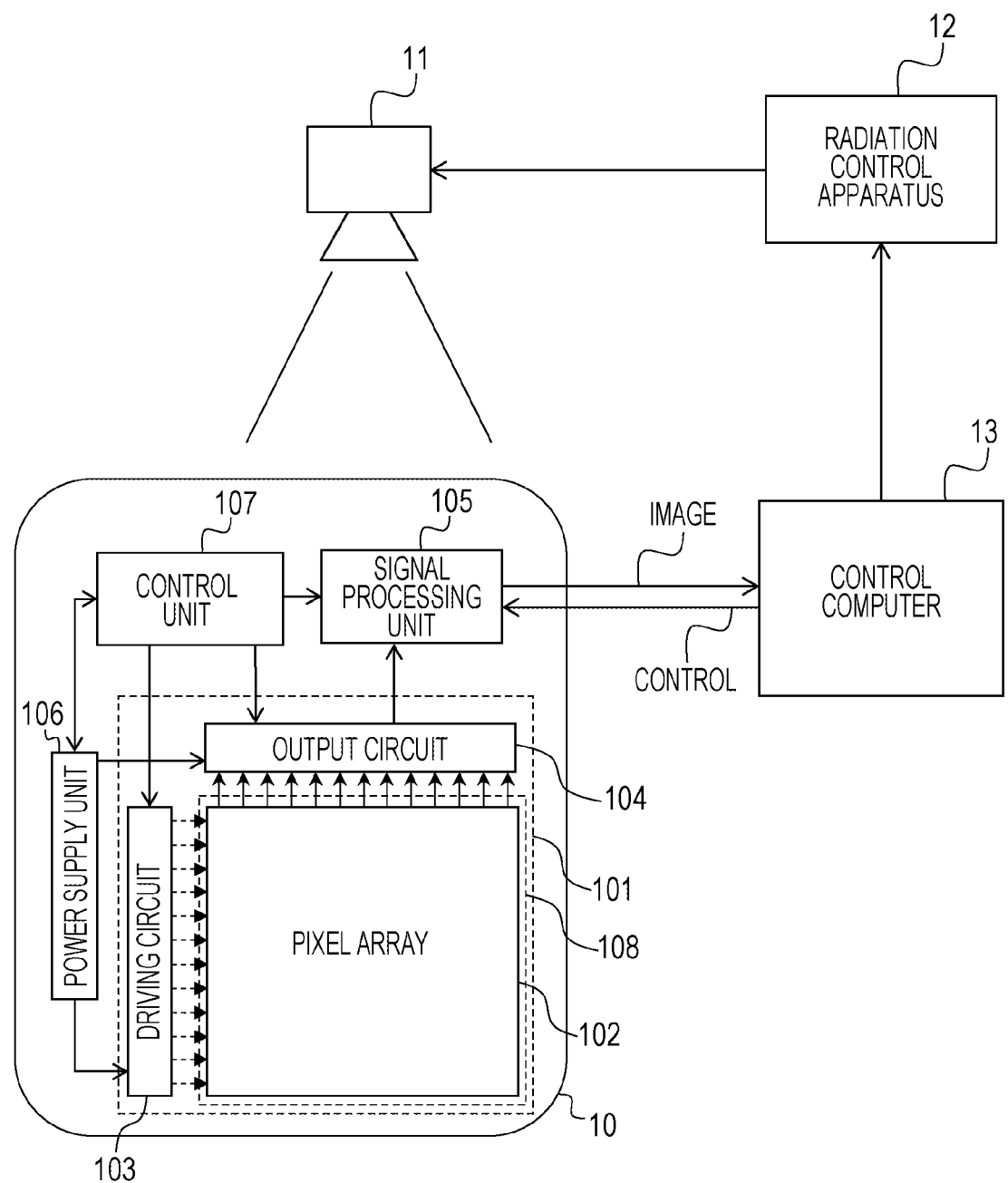

RADIATION IMAGING SYSTEM, SIGNAL PROCESSING APPARATUS, AND SIGNAL PROCESSING METHOD FOR RADIOGRAPHIC IMAGE

CROSS-REFERENCE TO RELATED APPLICATIONS

This application is a continuation of International Patent Application No. PCT/JP2016/004707, which was filed on Oct. 26, 2016 and which claims priority to Japanese Patent Application No. 2015-228012, which was filed on Nov. 20, 2015, both of which are hereby incorporated by reference in their entireties.

TECHNICAL FIELD

The present invention relates to a medical image diagnostic apparatus, a nondestructive inspection apparatus, a radiation imaging system applied to an analytical apparatus using radiation or the like, a signal processing apparatus, and a signal processing method for a radiographic image.

BACKGROUND ART

As an image pickup apparatus used for a medical image diagnosis based on radiation (X rays) or a nondestructive inspection, a radiation imaging apparatus using a flat panel detector (hereinafter, will be referred to as FPD) including a semiconductor element formed of a semiconductor material has been proposed. The above-described radiation imaging apparatus may be used as a digital image pickup apparatus for a still image, video, or the like in a medical image diagnosis, for example.

As the radiation imaging apparatus, a radiation imaging apparatus having an energy resolution has been proposed. For example, a photon counting type radiation imaging apparatus is configured to distinguish energy (wave length) of incident radiation and count the number of radiation detections in each of a plurality of energy levels. That is, a photon counting type sensor has an energy resolution and can be expected to be applied to discrimination of a substance, generation of an image in a case where shooting is performed by virtually using radiation of single energy, measurement of a density of bone, or the like. A detector including a conversion unit configured to convert radiation photons into optical photons or charges and a semiconductor element configured to obtain a pixel value in accordance with the optical photons or charges is used as the above-described radiation imaging apparatus having the energy resolution.

The radiation imaging apparatus having the energy resolution has an issue that the energy resolution is decreased by secondary radiation generated at the time of absorption of the radiation. PTL 1 describes a correction method of adding a value obtained by multiplying a measured value in a high energy band by a predetermined coefficient to the measured value in the high energy band and subtracting the value obtained by multiplying the measured value in the high energy band by the predetermined coefficient from a measured value in a low energy band. That is, while an error based on the secondary radiation having the lower energy than the incident radiation is taken into account, PTL 1 describes a technique for reducing the error based on the secondary radiation by adding a value obtained by multiplying the measured value in the high energy band obtained in accordance with the incident radiation by a predetermined coefficient corresponding to the error.

CITATION LIST

Patent Literature

PTL 1: Japanese Patent Laid-Open No. 63-171387

SUMMARY

Solution to Problem

However, in the radiation imaging apparatus including the detector including the conversion unit and the semiconductor element, a sufficient correction not performed on the basis of only the error based on the secondary radiation, and it is insufficient to suppress the decrease in the energy resolution. In view of the above, the present invention provides a technology for suppressing the decrease in the energy resolution with respect to the radiation imaging apparatus including the detector including the conversion unit and the semiconductor element.

A radiation imaging system according to an aspect of the present invention includes a detector including a conversion unit configured to convert incident radiation photons into optical photons or charges, a pixel array including pixels arranged in a two-dimensional matrix and configured to obtain a pixel value in accordance with the optical photons or charges, and an output circuit including a plurality of output channels configured to output the pixel value from the pixel array, and a signal processing unit configured to perform signal processing of correcting the pixel value by using a correction coefficient in accordance with a pixel value obtaining process model in which a process of obtaining the pixel value output from the pixel array via the plurality of output channels on the basis of the optical photons or charges is modeled and obtaining an energy-discriminated radiographic image based on the corrected pixel value. A signal processing apparatus according to an aspect of the present invention is configured to perform signal processing of performing correction by using a pixel value obtained in accordance with optical photons or charges converted from radiation photons incident on a detector including a conversion unit configured to convert incident radiation photons into optical photons or charges, a pixel array including pixels arranged in a two-dimensional matrix and configured to obtain a pixel value in accordance with the optical photons or charges, and an output circuit including a plurality of output channels configured to output the pixel value from the pixel array and obtaining an energy-discriminated radiographic image obtained on the basis of the corrected pixel value, by using a correction coefficient in accordance with a pixel value obtaining process model in which a process of obtaining the pixel value output from the pixel array via the plurality of output channels on the basis of the optical photons or charges is modeled. A signal processing method according to an aspect of the present invention includes performing signal processing of performing correction by using a pixel value obtained in accordance with optical photons or charges converted from radiation photons incident on a detector including a conversion unit configured to convert incident radiation photons into optical photons or charges, a pixel array including pixels arranged in a two-dimensional matrix and configured to obtain a pixel value in accordance with the optical photons or charges, and an output circuit including a plurality of output channels configured to output the pixel value from the pixel array and obtaining an energy-discriminated radiographic image obtained on the basis of the corrected pixel value, by using a correction coefficient in accordance with a pixel value obtaining process model in which a process of obtaining the pixel value output from the pixel array via the plurality of output channels on the basis of the optical photons or charges is modeled. In addition, a radiation imaging system according to an aspect of the present invention includes a flat panel detector including a conversion unit configured to convert incident radiation photons into optical photons or charges and a semiconductor element configured to obtain a pixel value in accordance with the optical photons or charges, and a signal processing unit configured to perform signal processing of correcting the pixel value by using a correction coefficient in accordance with a pixel value obtaining process model in which a processing of obtaining the pixel value on the basis of the optical photons or charges is modeled and obtaining an energy-discriminated radiographic image based on the corrected pixel value.

Advantageous Effects of Invention

According to the embodiment of the present invention, it becomes possible to suppress the decrease in the energy resolution with respect to the radiation imaging apparatus including the detector including the conversion unit and the semiconductor element.

Further features of the present invention will become apparent from the following description of exemplary embodiments with reference to the attached drawings.

BRIEF DESCRIPTION OF DRAWINGS

FIG. 1 is a schematic block diagram of a radiation imaging system.

DESCRIPTION OF EMBODIMENTS

Figure 2A:
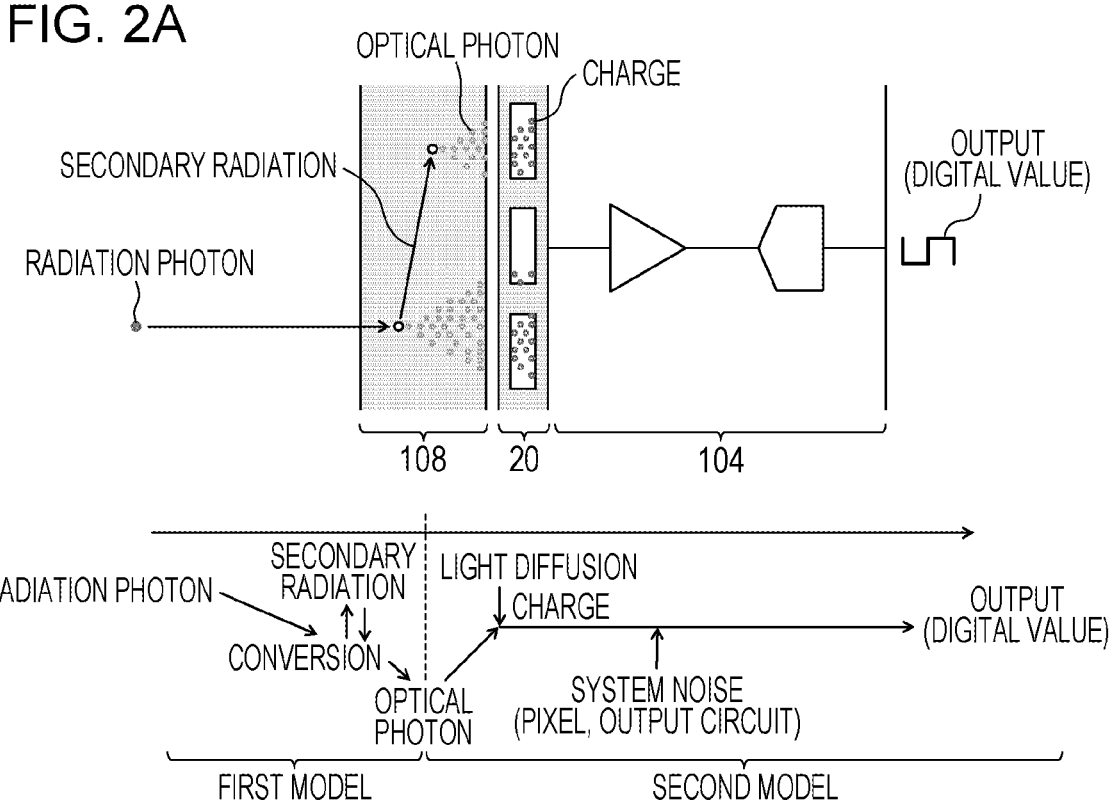
FIG. 2A is a conceptual view for describing a concept.

Hereinafter, embodiments of the present invention will be specifically described with reference to the accompanying drawings. It should be noted that, typically, radiation may be X rays but may also be $\alpha$ rays, $\beta$ rays, $\gamma$ rays, or the like.

First, a radiation imaging system will be described with reference to FIG. 1. FIG. 1 is a schematic block diagram of the radiation imaging system.

The radiation imaging system may include a radiation imaging apparatus 10, a control computer 13, a radiation control apparatus 12, and a radiation generating apparatus 11. The radiation imaging apparatus 10 may include a detector 101, a signal processing unit 105, a power supply unit 106, and a control unit 107. The detector 101 may include a conversion unit 108 configured to convert radiation into charges or light and a pixel array 102 in which a plurality of pixels configured to convert the charges or light converted by the conversion unit 108 into an electric signal are arranged in a two-dimensional matrix. The detector 101 may further include a driving circuit 103 configured to drive the pixel array 102 and an output circuit 104 configured to output an electric signal from the driven pixel array 102. It should be noted that examples of the detector 101 and the pixel will be described below in detail with reference to FIG. 8 and FIGS. 9A and 9B. The radiation imaging system and the control computer 13 according to the embodiment of the present invention obtain an energy-discriminated radiographic image on the basis of a signal from the pixel.

The control computer 13 supplies a control signal to the radiation imaging apparatus 10 and the radiation control apparatus 12 on the basis of shooting information input from a photographer (not illustrated) via a control console (not illustrated) of the control computer 13. The radiation control apparatus 12 receives the control signal from the control computer 13 and performs control of an operation of outputting radiation from a radiation source (not illustrated) of the radiation generating apparatus 11 and control of an operation of an irradiation field diaphragm mechanism (not illustrated). The control unit 107 of the radiation imaging apparatus 10 receives the control signal from the control computer 13 and performs control of the respective units of the radiation imaging apparatus 10. The detector 101 of the radiation imaging apparatus 10 outputs a signal in accordance with radiation output from the radiation generating apparatus 11 controlled by the radiation control apparatus 12. The output image signal is subjected to related-art signal processing by the signal processing unit 105 and is then transmitted to the control computer 13. Herein, a wireless communication or wired communication in a related art may be applied to the transmission. The transmitted image signal is subjected to necessary image processing by the control computer 13, and thereafter the energy-discriminated radiographic image may be displayed on a display unit (not illustrated) of the control computer 13.

Figure 2B:
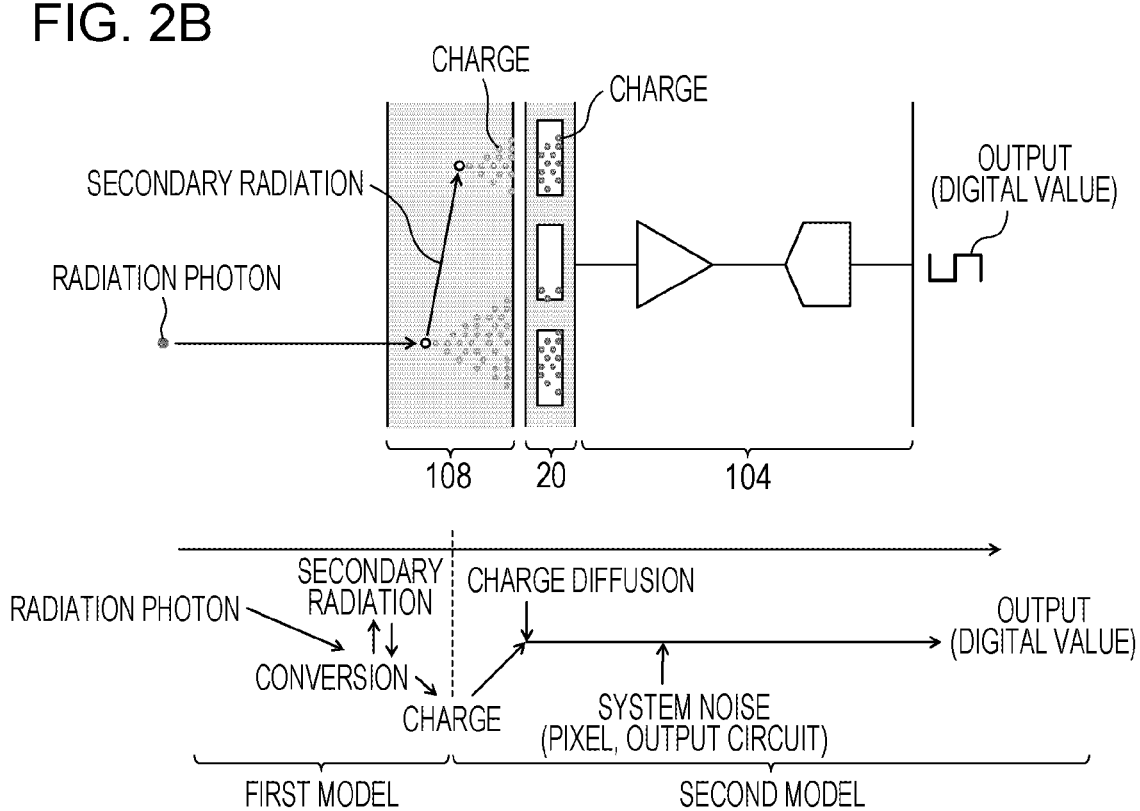
FIG. 2B is a conceptual view for describing the concept.

Next, a concept of the embodiment of the present invention will be described with reference to FIG. 2A and FIG. 2B. FIG. 2A is a conceptual diagram for describing the concept of the embodiment of the present invention in a case where an indirect type radiation imaging apparatus using a scintillator and a photoelectric conversion apparatus is used. FIG. 2B is a conceptual diagram for describing the concept of the embodiment of the present invention in a case where a direct type radiation imaging apparatus configured to directly convert radiation into charges is used.

First, in the radiation imaging apparatus illustrated in FIG. 2A, incident radiation photons are converted into optical photons when being absorbed by the scintillator serving as the conversion unit 108. At this time, in a case where the radiation photons have energy higher than or equal to predetermined energy of the scintillator, secondary radiation having lower energy than the incident radiation may be generated. Descriptions will be given while predetermined energy at which this secondary radiation may be generated will be hereinafter referred to as excitation energy. The generated secondary radiation separately generates optical photons. On the other hand, in the radiation imaging apparatus illustrated in FIG. 2B, the incident radiation photons are converted into charged when being absorbed by a conversion film made of cadmium telluride (CdTe) or the like serving as the conversion unit 108. At this time, in a case where the radiation photons have energy higher than or equal to the excitation energy of the conversion film, the secondary radiation having energy lower than the incident radiation may be generated. The generated secondary radiation separately generates charges. That is, when the incident radiation photons are absorbed by the conversion unit 108 and converted into the optical photons or charges, in a case where the incident radiation has energy higher than or equal to the excitation energy of the conversion unit 108, the still lower secondary radiation may be generated. The generated secondary radiation separately generates optical photons or charges by the conversion unit 108. Energy of part of the radiation photons among the incident radiation photons is converted into photons or charges based on the secondary radiation having the lower energy by the optical photons or charges separately generated by the secondary radiation. As a result, such an error may occur that the energy of the part of the radiation photons is shifted to an output having the lower energy. A model of the error occurrence thus far will be hereinafter referred to as a photon conversion process model.

Next, in the radiation imaging apparatus illustrated in FIG. 2A, the optical photons generated by the scintillator serving as the conversion unit 108 may diffuse before reaching a pixel 20 or may reach an adjacent pixel 20, for example, which is different from the pixel 20 where the optical photons are originally intended to reach. In addition, in the radiation imaging apparatus illustrated in FIG. 2B, the charges generated by the conversion film serving as the conversion unit 108 may diffuse before reaching the pixel 20 and reach the adjacent pixel 20, for example, which is different from the pixel 20 where the optical photons are originally intended to reach in some cases. In the above-described case, a signal based on the optical photons or charges that have reached the other pixel 20 decreases a signal of the pixel where the optical photons are originally intended to reach and increases a signal of the other pixel 20. Semiconductor elements constituting the respective elements of the detector 101 configured to obtain a pixel value in accordance with the incident radiation photons have noise that causes a temporal and/or spatial output variation such as KTC noise or flicker noise. In addition, each of the pixels 20 has its own intrinsic noise. The output circuit 104 has an individual circuit for each of the output channels of the pixel array 102, and each of the individual circuits has its own intrinsic noise. Furthermore, a so-called sensitivity variation where sensitivities of the plurality of pixels 20 are varied may occur because of characteristic variations of the respective elements of the plurality of pixels 20. According to this, the signals output from the respective pixels include so-called fixed pattern noise where the respective intrinsic sensitivity variations are combined with the noise or system noise including the temporal and/or spatial output variation of the semiconductor elements. The fixed pattern noise, the system noise, and the diffusion of the optical photons or charges may cause the variation in the signal from the detector, and an error due to the variation may occur. That is, a model in which an error may occur during a process of obtaining a radiographic image based on the pixel value corresponding to the signals output from the respective pixels 20 on the basis of the optical photons or charges generated by the conversion unit 108 will be hereinafter referred to as a pixel value obtaining process model.

That is, in the radiation imaging apparatus including the conversion unit 108 and the semiconductor element, the errors caused by the variation which may be generated in the pixel value obtaining process model need to be applied to the processing of correcting the energy-discriminated radiographic image. In view of the above, signal processing for correcting the energy-discriminated radiographic image is performed on the basis of the pixel value by using the correction coefficient in accordance with the pixel value obtaining process model in which the process of obtaining the pixel value on the basis of the optical photons or charges generated by the conversion unit 108 is modeled. That is, the processing of correcting the energy-discriminated radiographic image is performed by using the correction coefficient in accordance with the diffusion of the optical photons or charges generated by the conversion unit 108, the fixed pattern noise of the detector 101 which may be added to the signal from the pixel array 102, and the system noise. According to this, it is possible to suppress the error that may occur in the energy-discriminated radiographic image based on the pixel value which is caused by the error that may occur in the above-described pixel value obtaining process model and suppress the decrease in the energy resolution. Then, the error caused by the secondary radiation which may occur in the above-described photon conversion process model is further applied to the processing of correcting the energy-discriminated radiographic image. For this reason, the correction coefficient can be prepared such that the correction coefficient used for the processing of correcting the energy-discriminated radiographic image can correspond to the secondary radiation that may be generated during the process in which the incident radiation photons are converted into the optical photons or charges. Accordingly, moreover, it is possible to suppress the error that may occur in the energy-discriminated radiographic image which is caused by the error that may occur in the above-described photon conversion process model and further suppress the decrease in the energy resolution. It should be noted that the secondary radiation generated in the conversion unit 108 is used as an example in the following descriptions, but the embodiment of the present invention is not limited to this. For example, scattered radiation generated in an object or the like may also be regarded as the secondary radiation in a broad sense.

Next, the photon conversion process model and the pixel value obtaining process model used for the calculation of the above-described correction coefficient will be described in detail with reference to FIGS. 3A to 3D and FIGS. 4A to 4C. It should be noted that the indirect type radiation imaging apparatus is used as an example in FIGS. 3A to 3D and FIGS. 4A to 4C.

Figure 3A:
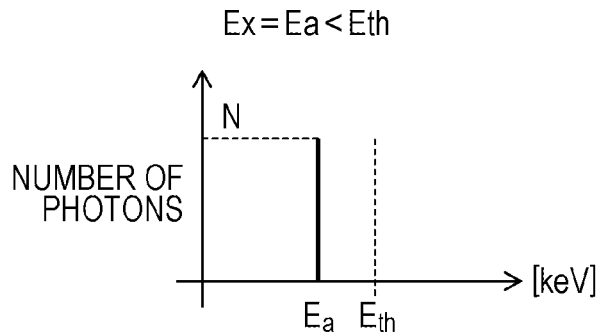
FIG. 3A is a schematic diagram illustrating a spectrum for describing the concept.
Figure 3B:
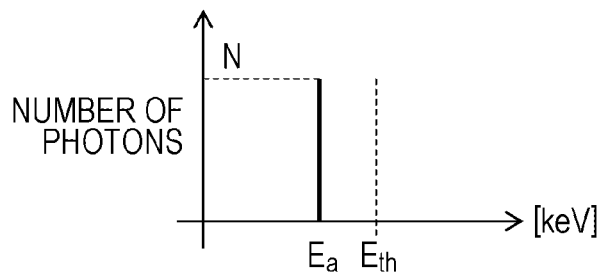
FIG. 3B is a schematic diagram illustrating the spectrum for describing the concept.
Figure 3C:
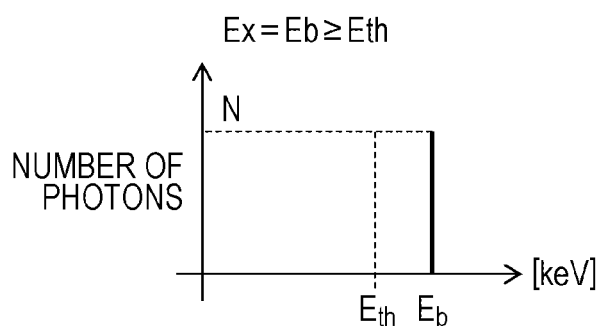
FIG. 3C is a schematic diagram illustrating the spectrum for describing the concept.
Figure 3D:
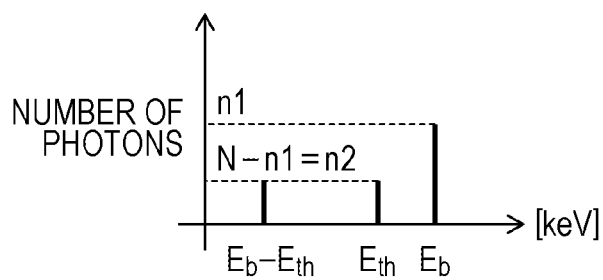
FIG. 3D is a schematic diagram illustrating the spectrum for describing the concept.

First, a concept of the photon conversion process model will be described with reference to FIGS. 3A to 3D. Herein, FIGS. 3A to 3D are schematic diagram illustrating a spectrum for describing the concept of the photon conversion process model. As illustrated in FIG. 3A, in a case where the radiation photons having energy $E_a$ lower than excitation energy $E_{th}$ are incident on the N conversion units 108, the outputs from the conversion units 108 become the desired number of optical photons in which the N radiation photons having the energy $E_a$ are maintained as illustrated in FIG. 3B. It should be noted that, to simplify the descriptions herein, it is represented by the number of the radiation photons corresponding to the desired number of optical photons. On the other hand, as illustrated in FIG. 3C, in a case where the radiation photons having energy $E_b$ higher than the excitation energy $E_{th}$ are incident on the N conversion units 108, as described above, the secondary radiation may be generated from part of the radiation photons. As illustrated in FIG. 3D, the optical photons corresponding to the $n_1$ radiation photons having the energy $E_b$ among the N radiation photons are obtained. In addition, the optical photons corresponding to the $n_2$ (=N−$n_1$) radiation photons of the excitation energy and the optical photons corresponding to the $n_2$ radiation photons having energy corresponding to a difference between the energy $E_b$ and the excitation energy $E_{th}$ (=$E_b$−$E_{th}$) may be generated. That is, the error caused by the secondary radiation can be modeled as the photon conversion process model while the excitation energy $E_{th}$ of the conversion unit 108 and a generation ratio ($n_1$/N) of the optical photons corresponding to the energy $E_b$ of the incident radiation are used as the parameters.

Here, the modeling of the photon conversion process model will be specifically described below. First, a simulation with respect to the secondary radiation is performed. Herein, energy of the radiation photons incident on the conversion units is set as $E_x$, the number of the radiation photons having the energy $E_x$ is set as $P_x(E_x)$, the generation ratio of the secondary radiation is set as $X_p$, and the excitation energy is set as $E_{th}$. It should be noted that the energy is saved in the following descriptions for simplicity.

It is assumed that the radiation photons incident on the conversion units generate the secondary radiation at a probability of $X_p$. In a case where the secondary radiation is not generated, it is assumed that all the energy of the radiation photons is transferred to photoelectrons in the conversion units. In this case, when energy of the photoelectrons is set as $E_n$, $E_n=E_x$ is established. In a case where secondary X rays are generated, it is assumed that the excitation energy $E_{th}$ of the secondary X rays among the energy $E_x$ of the radiation photons is transferred to the secondary X rays, and the remaining energy is transferred to the photoelectrons. In addition, it is assumed that the generated energy of the secondary X rays is transferred to the other photoelectrons. That is, the radiation photons having the energy $E_x$ are converted into the photoelectrons having the energy $E_n=E_x-E_{th}$ and the photoelectrons having the energy $E_n=E_{th}$. Thus, the number $P_s(E_n)$ of the photoelectrons having the energy $E_n$ generated in the conversion units is represented by the following expressions (1) to (3).

In the case of $E_x<E_{th}$, the following expression is adopted.
[Math. 1]

$$P_s(E_n)=P_x(E_x)+X_p*P_x(E_x+E_{th}) \quad (1)$$

Where $P_x(E_x+E_{th})$ means the number of the radiation photons having the energy $E_x+E_{th}$.

In the case of $E_x=E_{th}$, the following expression is adopted,

[Math. 2]

$$P_s(E_n) = P_x(E_x) + X_p * \sum_{E=E_{th}}^{\infty} P_x(E) \quad (2)$$

Where $\Sigma P_x(E)$ means a total sum of the number of the radiation photons that satisfy the energy $E>E_{th}$.

In the case of $E_x>E_{th}$, the following expression is adopted.
[Math. 3]

$$P_s(E_n)=(1-X_p)*P_x(E_x)+X_p*P_x(E_x+E_{th}) \quad (3)$$

While calculations using the above-described expressions (1) to (3) are performed with respect to the energy $E_x$ of all the radiation photons, a histogram of the number $P_s(E_n)$ of the photoelectrons is created. It should be noted that, in the above-described expressions (1) to (3), it is supposed that the secondary radiation is generated only once, but the embodiment of the present invention is not limited to the above-described supposition. For example, in a case where the energy $E_x$ of the radiation photons exceeds $2E_{th}$, such a supposition that the second secondary radiation is generated may be established. The thus generated photoelectrons are converted into the number of the optical photons or charges proportional to the energy $E_n$. The simulation with respect to the secondary radiation is performed in the above-described manner, and the modeling of the photon conversion process model may be performed.

Figure 4A:
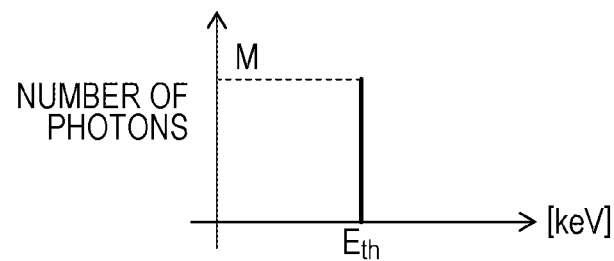
FIG. 4A is a schematic diagram illustrating the spectrum for describing the concept.
Figure 4B:
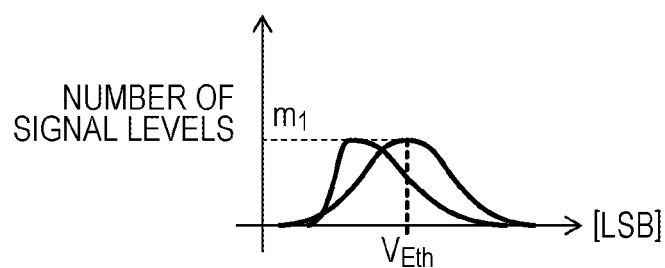
FIG. 4B is a schematic diagram illustrating the spectrum for describing the concept.
Figure 4C:
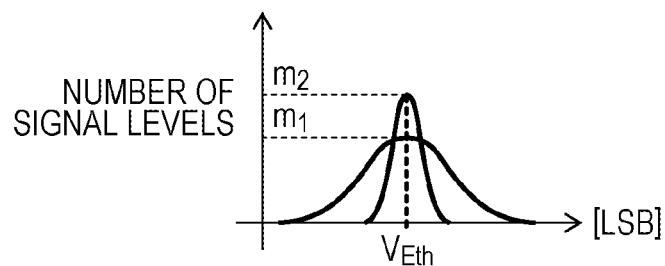
FIG. 4C is a schematic diagram illustrating the spectrum for describing the concept.

Next, a concept of the pixel value obtaining process model will be described with reference to FIGS. 4A to 4C. Herein, FIG. 4A is a schematic diagram illustrating a histogram of the optical photons incident on the pixel array 102 in which a horizontal axis represents the energy of the optical photons incident on the pixel array 102, and a vertical axis represents the number of the optical photons. In addition, FIG. 4B and FIG. 4C are schematic diagrams illustrating a histogram representing a spectrum of an output level of the pixel array in which a horizontal axis represents a signal level output from the pixel array 102, and a vertical axis represents the number of the respective signal levels. As illustrated in FIG. 4B and FIG. 4C, the above-described two types of errors appear in a shape of the histogram (shape of the output variation) and a size of the histogram (size of the output variation). As illustrated in FIG. 4B, a width of the variation may be represented as a shape of a bilaterally-symmetric chevron having a certain peak at the center, a shape of a bilaterally-asymmetric chevron in which the center of the peak is deviated, or the like. In addition, as illustrated in FIG. 4C, even when a position of the peak is the same, the size of the peak varies. In the above-described manner, a size (degree) of the variation may be represented on the basis of the size of the peak. Herein, since the numbers of incident photons are equal to each other, the width of the peak is decreased as the size of the peak is larger. In the above-described manner, the size of the peak and the width have a predetermined correlation relationship. That is, the above-described two types of errors can be modeled as the pixel value obtaining process model while the shape of the histogram (shape of the output variation) and the size of the histogram (size of the output variation) are used as the parameters.

Here, the modeling of the pixel value obtaining process model will be specifically described below. A signal is generated by the pixel 20 in accordance with the optical photons or charges converted by the conversion units, and a signal level in accordance with the number of the optical photons or charges is obtained. That is, when a signal level in accordance with the photoelectrons having energy $E_m$ is set as $S_m$, a signal level $S_n$ in accordance with the photoelectrons having energy $E_n$ is represented by the following expression (4).
[Math. 4]

$$E_m/S_m = E_n/S_n \quad (4)$$

When the expression (4) is transformed, the following expression (5) is obtained.
[Math. 5]

$$E_n = S_n * E_m/S_m \quad (5)$$

When the number of signal levels $S_n$ is set as $N_x (S_n)$ $N_x (S_n)$ is equal to the number $P_s (E_n)$ of the photoelectrons having the energy $E_n$. Therefore, $N_x (S_n)$ is represented by the following expression (6).
[Math. 6]

$$N_x(S_n) = P_s(E_n) = P_s(S_n * E_m/S_m) \quad (6)$$

Where each of the above-described expressions (1) to (3) may be applied to $P_s (S_n \times E_n/S_m)$.

Herein, when the optical photons or charges are converted into the signal levels, a variation of the signal levels need to be taken into account. A shape of the histogram of this variation (shape of the output variation) is supposed to be a normal distribution. According to this, the size of the histogram (size of the output variation) can be represented by a standard deviation σ of the variation of the signal levels. That is, when a parameter of the signal levels is set as S, the number $N_s (S_n)$ of the signal levels $S_n$ in which the variation of the signals is taken into account is represented by the following expression (7).

[Math. 7]

$$N_s(S_n) = \sum_{s=0}^{\infty} \left\{ N_x(S) \frac{1}{\sqrt{2\pi\sigma^2}} \exp\left(-\frac{(S_n - S)^2}{2\sigma^2}\right) \right\} \quad (7)$$

Where the above-described expression (6) is applied to $N_x (S)$. In addition, an actually measured value is used as a signal level $S_m$ in a case where the radiation photons having the energy $E_m$ are incident and the standard deviation σ of the variation of the signal levels among the parameters used in this calculation. Specifically, radiation including only the single energy $E_m$ is input to measure the histogram of the signal levels. An average value of this histogram is set as the signal level $S_m$ in a case where the radiation photons having the energy $E_m$ are incident, and the standard deviation of the histogram is set as the standard deviation σ of the variation of the signal levels. It should be noted that the energy $E_m$ of the radiation input at this time is preferably lower than generated the excitation energy $E_{th}$ by the secondary radiation.

Thus, the calculation is performed with respect to all the signal levels Sn by using the expressions (1) to (7) so that a virtual histogram in which the horizontal axis represents the signal level output from the pixel array 102 and the vertical axis represents the number of respective signal levels may be created.

Figure 5A:
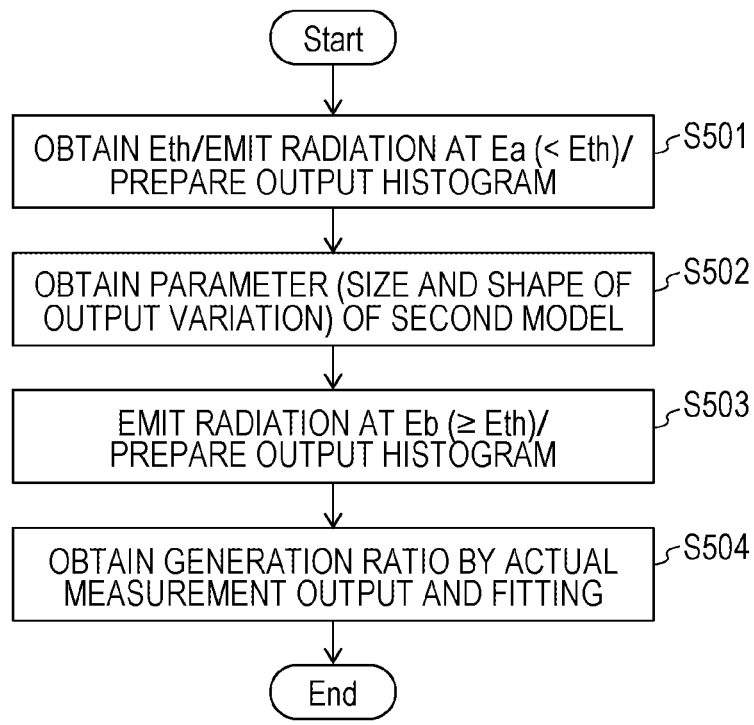
FIG. 5A is a flow chart.

Next, a modeling method for the photon conversion process model and the pixel value obtaining process model will be described with reference to FIG. 5A. FIG. 5A is a flow chart for deviating respective parameters of the photon conversion process model and the pixel value obtaining process model. The modeling of the photon conversion process model and the pixel value obtaining process model is performed by deviating the above-described respective parameters.

First, a shape of a spectrum (shape of the output variation) and a size of the spectrum (size of the output variation) corresponding to the parameters of the pixel value obtaining process model may be previously measured and obtained by the following method. In S501, the radiation imaging apparatus is irradiated with radiation having the energy $E_a$ that is lower than the excitation energy, and signals output from the radiation imaging apparatus at this time are obtained to prepare a histogram of the signals. Specifically, radiation including only the single energy $E_m$ is input to measure a histogram of the signal levels. It should be noted that the excitation energy $E_{th}$ of the conversion unit 108 corresponding to the parameter of the photon conversion process model depends on a material of the conversion unit 108. For this reason, information related to the excitation energy may be previously obtained. For example, in a case where cesium iodide (CsI) is used as the scintillator used in the example illustrated in FIG. 2A, the excitation energy is approximately 30 KeV. Next, in S502, information related to a size of the output variation may be obtained from a half power width of the peak of the histogram. In addition, information related to a shape of an output variation may be obtained from the distribution of the histogram or the shape of the measured value. A standard deviation of the variation of the signal levels is set as σ, and an average of the signal levels is set as S as the parameters of the shape of the spectrum (shape of the output variation) and the size of the spectrum (size of the output variation). Then, the average value of this histogram may be set as the signal level $S_m$ in a case where the radiation photons having the energy $E_m$ are incident, and the standard deviation of the histogram may be set as the standard deviation σ of the variation of the signal levels. In the above-described manner, the respective parameters of the pixel value obtaining process model may be derived in S502.

Next, in S503, the radiation imaging apparatus is irradiated with radiation having the energy $E_b$ that is higher than or equal to the excitation energy to measure signals output from the radiation imaging apparatus at this time, and a histogram of the signals is prepared.

Next, in S504, the generation ratio is set as a variable value, and the virtual histogram in which the horizontal axis represents the signal level output from the pixel array 102 and the vertical axis represents the number of respective signal levels is generated by using the other parameters that have been already obtained. Herein, for example, by applying the above-described expressions (1) to (5), the generation ratio $X_p$ is set as a variable value, and a virtual histogram may be generated. Subsequently, fitting of the histogram actually measured in S503 and the virtual histogram is performed so as to establish a state in which the histogram and the virtual histogram are closest to each other by varying the generation ratio, and a value at which the state in which the histogram and the virtual histogram are closest to each other (including matching) is established may be obtained as information related to the generation ratio. In the above-described manner, the respective parameters of the photon conversion process model in S504 may be derived. It should be noted that, herein, the histogram of the signals obtained when the radiation imaging apparatus is irradiated with the radiation having the energy lower than the excitation energy is prepared, but the embodiment of the present invention is not limited to this. For example, a conversion efficiency of the radiation in the direct type radiation imaging apparatus is higher than that of the indirect type radiation imaging apparatus, and accordingly, an S/N ratio is higher than that of the indirect type radiation imaging apparatus. For this reason, the peak of the incident radiation and the peak of the secondary radiation may be separated from each other in the histogram of the signals obtained when the direct type radiation imaging apparatus is irradiated with the radiation having the energy higher than or equal to the excitation energy. For this reason, since the direct type radiation imaging apparatus can obtain the above-described parameter with respect to the peak of the incident radiation, the radiation having the energy higher than or equal to the excitation energy may be used.

Figure 5B:
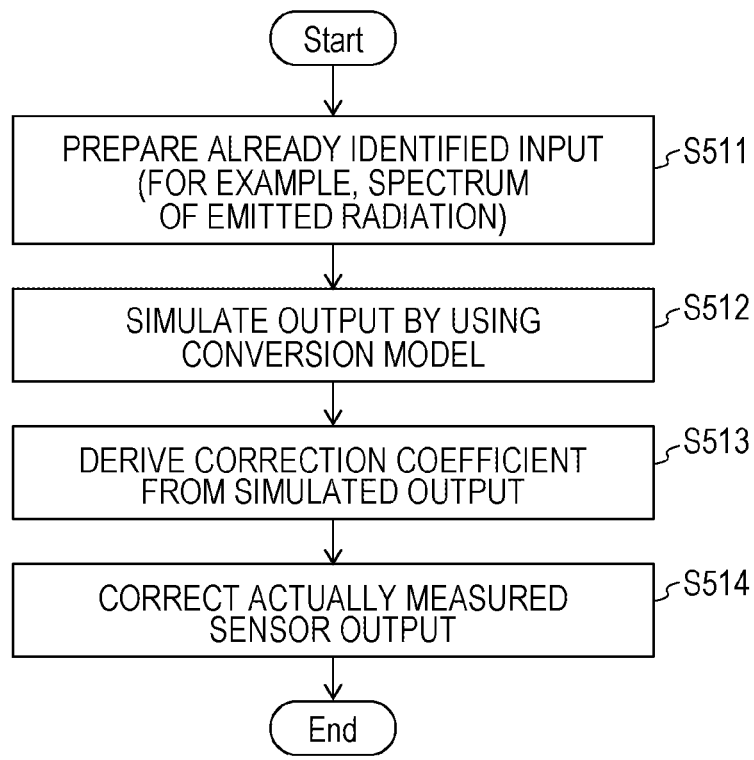
FIG. 5B is a flow chart.

Next, a correction method according to the embodiment of the present invention will be described with reference to FIG. 5B and FIGS. 6A to 6E. FIG. 5B is a flow chart for describing the correction method.

Figure 6A:
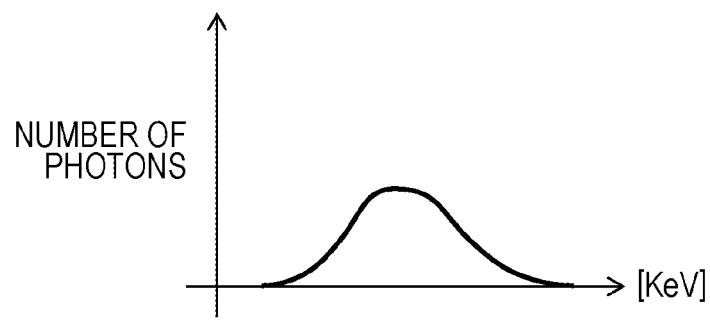
FIG. 6A is a schematic diagram illustrating the spectrum for describing the concept.
Figure 6B:
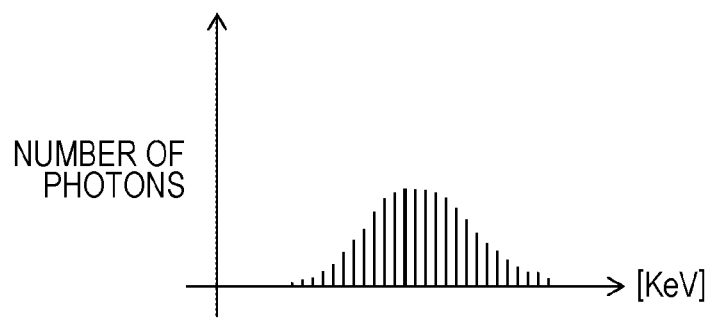
FIG. 6B is a schematic diagram illustrating the spectrum for describing the concept.
Figure 6C:
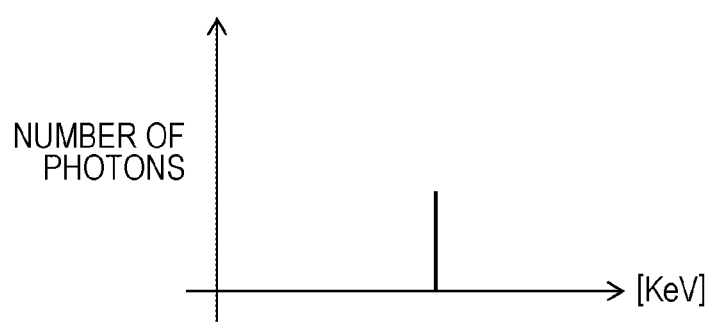
FIG. 6C is a schematic diagram illustrating the spectrum for describing the concept.
Figure 6D:
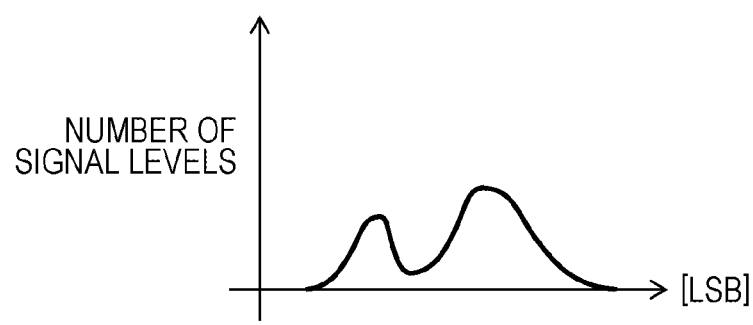
FIG. 6D is a schematic diagram illustrating the spectrum for describing the concept.
Figure 6E:
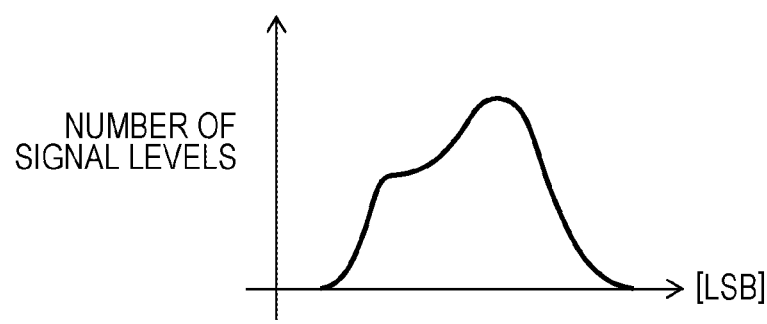
FIG. 6E is a schematic diagram illustrating the spectrum for describing the concept.
Figure 7A:
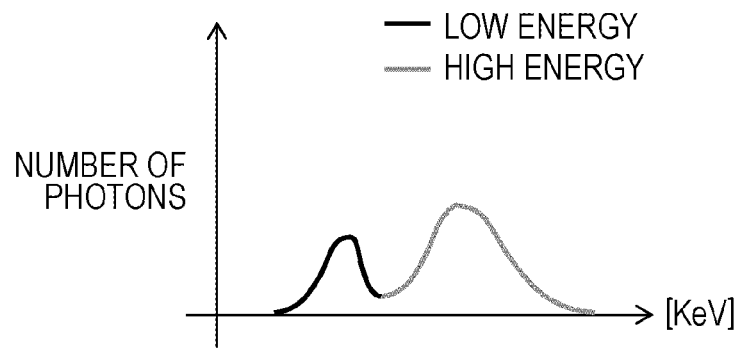
FIG. 7A is a schematic diagram illustrating the spectrum for describing the concept.
Figure 7B:
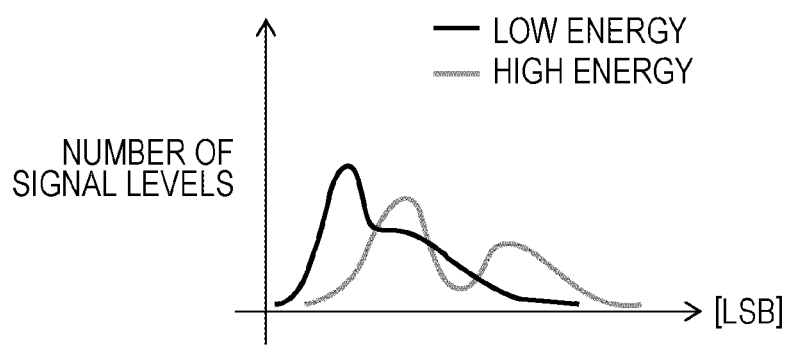
FIG. 7B is a schematic diagram illustrating the spectrum for describing the concept.

First, in S511, information related to the emitted radiation is obtained. Herein, a spectrum of the emitted radiation is used as the information related to the emitted radiation. This spectrum may be obtained by previously performing measurement using a spectrometer or the like. Then, as illustrated in FIG. 7A, while arbitrary energy is set as a threshold, energy is divided into a plurality of energy regions including, for example, two regions of a low energy region and a high energy region. It should be noted however that, as illustrated in FIG. 6A, since energy continuously exists in a mixed manner in the emitted radiation, as illustrated in FIG. 6B, the radiation is converted into a form of an aggregate having substantially single energy at a desired interval. This conversion is applied to each of the plurality of energy regions. Next, in S512, as illustrated in FIG. 6C, desired substantially single energy is extracted from the aggregate having the substantially single energy at the desired interval. This extraction is also applied to each of the plurality of energy regions and the entirety. Next, the photon conversion process model and the pixel value obtaining process model which have been previously modeled are applied to the extracted substantially single energy to simulate the output from the pixel 20 as illustrated in FIG. 6D. This simulation is also applied to each of the plurality of energy regions. That is, in FIG. 6D and FIG. 6E, a horizontal axis represents the signal level output from the pixel 20, and a vertical axis represents the number of the respective signal levels. Subsequently, similar processing is performed on the other substantially single energy of the aggregate having the substantially single energy at the desired interval, and respective simulation results are added to one another, so that the simulation results corresponding to the number of the respective signal levels of the output of the pixel 20 are obtained. This addition of the simulation results is also applied to each of the plurality of energy regions. According to this, as illustrated in FIG. 7B, each of the plurality of energy regions of the output of the radiation imaging apparatus and the simulation result of the entirety are obtained. It should be noted that, in the histogram illustrated in FIG. 7B, a horizontal axis represents the signal level output from the pixel 20, and a vertical axis represents the number of signal levels. Herein, the simulation result of the entirety may be obtained by adding the results of the plurality of energy regions to one another or obtained by performing the above-described respective processings on the entire spectrum of the radiation.

Next, in S513, a correction coefficient is derived from the simulation result obtained in S512. Herein, a correction coefficient α is a ratio of those attributable to the incident radiation photons of the low energy region with respect to the respective signal levels output from the pixel array 102. Specifically, the number of the signal levels of the plurality of energy regions is set as a denominator. The number of the signal levels attributable to the incident radiation photons of the low energy region is set as a numerator. That is, this means that the ratio of the incident radiation attributable to the radiation photons of the low energy region is α of the total, and the ratio of the incident radiation attributable to the radiation photons of the high energy region is (1−α) of the total among the outputs from the radiation imaging apparatus.

Figure 7C:
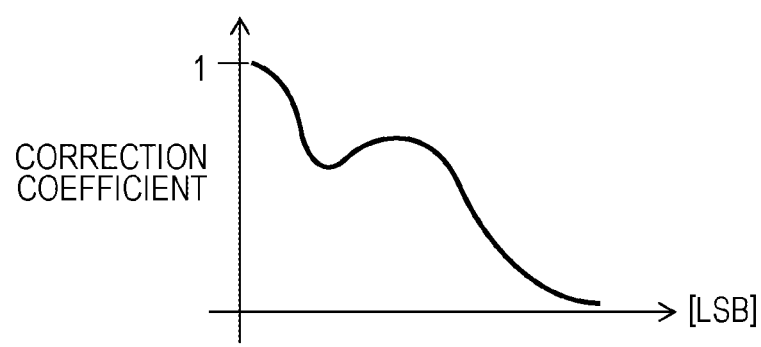
FIG. 7C is a schematic diagram illustrating the spectrum for describing the concept.

Next, in S514, correction is performed by applying the above-described correction coefficient to the number of the signal levels output from the pixel 20. In this example illustrated in FIG. 7C, in a case where the correction coefficient with respect to a certain signal level is set as α, a value obtained by multiplying the number of the signal levels by α is set as a counted value of the low energy region, and a value obtained by multiplying the number of the signal levels by (1−α) is set as a counted value of the high energy region. This process is performed with respect to all the signal levels, and a total of the counted value of the low energy region and a total of the counted value of the high energy region are obtained. While the correction is performed in the above-described manner, it is possible to correct the energy-discriminated radiographic image. According to this, it is possible to suppress the error that may occur in the energy-discriminated radiographic image caused by the error that may occur in the photon conversion process model and the pixel value obtaining process model and suppress the decrease in the energy resolution. It should be noted that the correction coefficient of the present invention is not limited to the above-described embodiment and may be a correction coefficient in which the ratio of the pixel numbers attributable to the incident radiation photons of the high energy region is set as a numerator, for example. In addition, in FIG. 7B and FIG. 7C, the descriptions have been given by using the configuration in which a large number of signal levels exist, but the number of the signal levels may be an arbitrary integer higher than or equal to 2. For example, a configuration may be used in which the output of the pixel 20 is converted into a digital value by using two thresholds.

Figure 8:
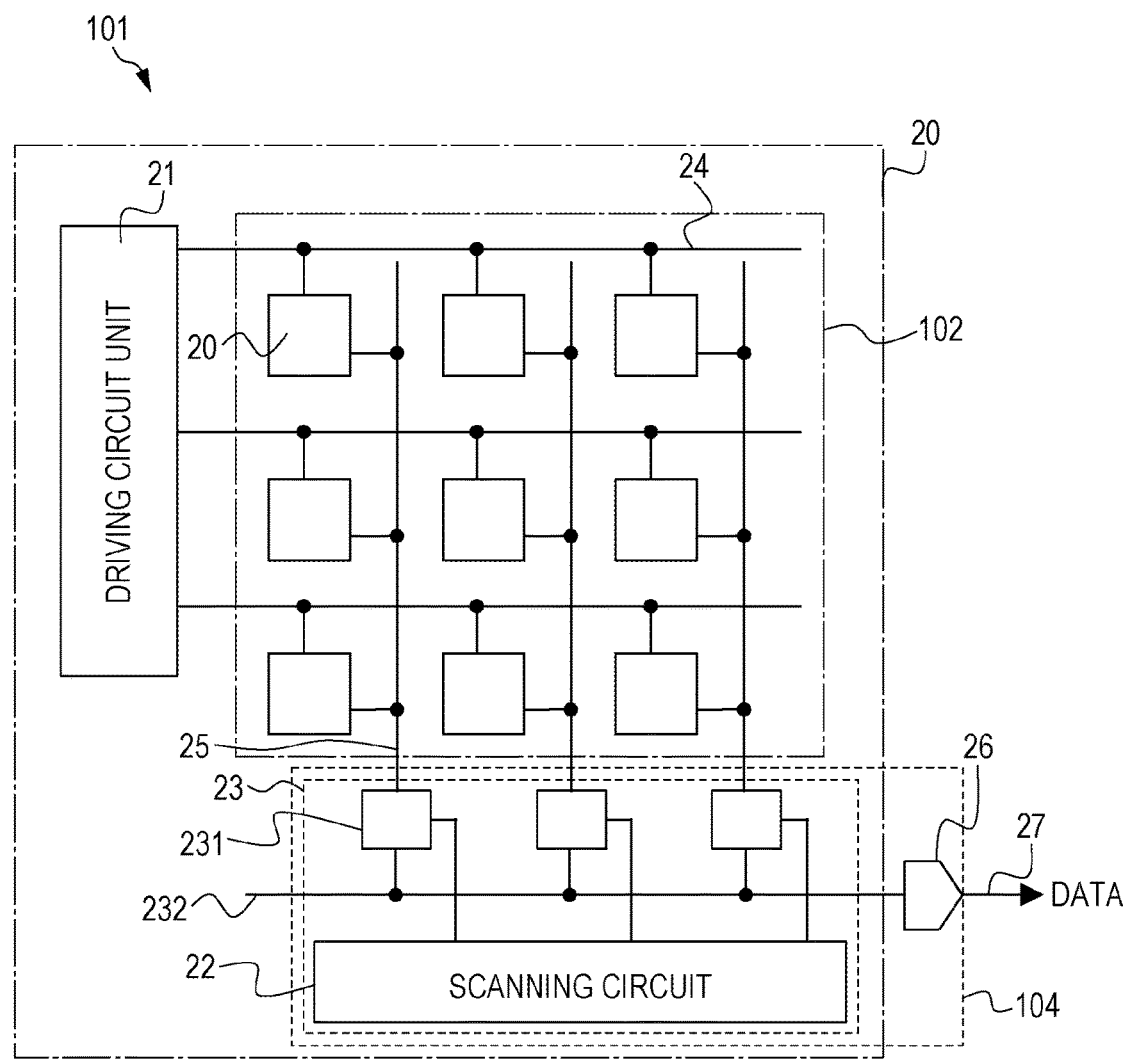
FIG. 8 is a block diagram illustrating a schematic configuration of an example of a detector.
Figure 9A:
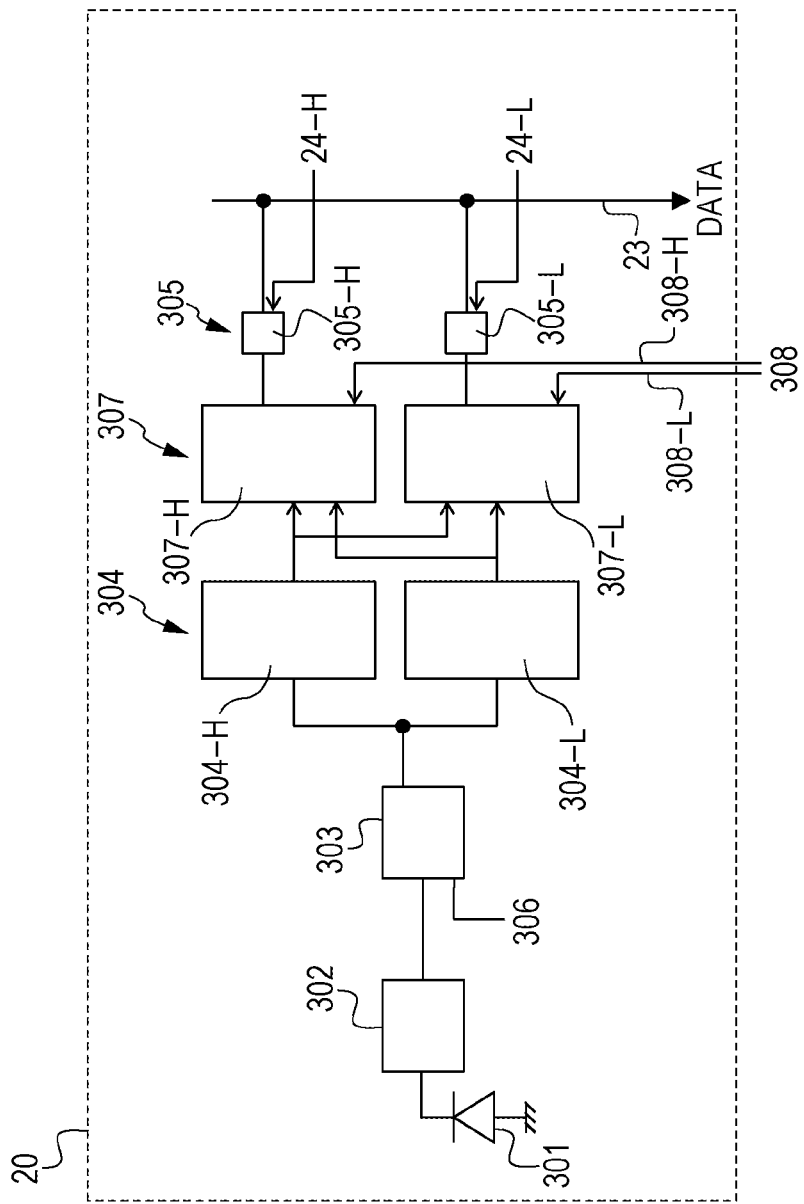
FIG. 9A is a block diagram illustrating a schematic configuration of an example of a pixel.

Hereinafter, an example of the detector 101 of the radiation imaging apparatus that may be applied to the embodiment of the present invention will be described with reference to the drawing. FIG. 8 is a block diagram illustrating a schematic configuration for describing the example of the detector 101.

In the pixel array 102, the conversion units configured to convert the incident radiation photons into the optical photons or charges and the plurality of pixels 20 configured to obtain a pixel value in accordance with electric signals based on the optical photons or charges are preferably arranged in a two-dimensional matrix.

A driving circuit unit 21 included in the driving circuit 103 is a circuit configured to supply respective driving signals via a driving wiring unit 24 and operate the pixel array 102 in units of a desired pixel group. According to the present embodiment, the driving circuit unit 21 is a circuit configured to operate a pixel circuit unit 202 of the plurality of pixels 20 in the pixel array 102 in units of a row. The driving wiring unit 24 may be a group of a plurality of driving wirings individually prepared for each of the respective driving signals.

A readout circuit unit 23 included in the output circuit 104 is a circuit unit configured to convert the electric signals output in parallel from the pixel array 102 via a signal line 25 into serial electric signals to be read out. The readout circuit unit 23 includes a selection switch 231, a scanning circuit 22, an output line 232, and an output buffer 233. It should be noted that the output circuit 104 further includes an analog-to-digital (A/D) converter 26 electrically connected to the output line 232 via an output unit 26, and the A/D converter 26 converts an analog image signal based on the electric signal output from the pixel array 102 into a digital image signal DATA. The digital image signal DATA is transmitted to the signal processing unit 105 via a transmission line 27.

Next, an example of the pixel 20 of the radiation imaging apparatus that may be applied to the embodiment of the present invention will be described with reference to the drawing. First, an example of the pixel 20 of the indirect and photon counting type radiation imaging apparatus will be described with reference to FIG. 9A. Each of the respective pixels 20 may include a photoelectric conversion element 301, a voltage conversion unit 302, a comparison unit 303, a correction unit 304, and an output unit 305. The photoelectric conversion element 301 detects light generated by the scintillator 108 when radiation is incident on the scintillator 108 and generates a signal. A photodiode or the like may be used as the photoelectric conversion element 301, for example. A differentiating circuit is used as the voltage conversion unit 302, for example. The voltage conversion unit 302 converts the signal generated by the photoelectric conversion element 301 into a pulse signal of a voltage and outputs the pulse signal to the comparison unit 303. The comparison unit 303 compares a voltage value of the pulse signal output from the voltage conversion unit 302 with a reference voltage 306 and generates, for example, a binary signal as a comparison result signal in accordance with a comparison result. In a case where the voltage value of the pulse signal output from the voltage conversion unit 302 is higher than or equal to a voltage value of the reference voltage 306, the comparison unit 303 outputs a digital value "1" as the signal in accordance with the comparison result. On the other hand, in a case where the voltage value of the pulse signal output from the voltage conversion unit 302 is lower than the reference voltage 306, the comparison unit 303 outputs a digital value "0" as the signal in accordance with the comparison result. The reference voltage 306 supplied to the comparison unit 303 may be set to have a common value with respect to all of pixels in the detector 101. When radiation is incident on the scintillator to be converted into light, the comparison unit 303 generates a signal having a binary digital value via the voltage conversion unit 302 in accordance with the light detected by the photoelectric conversion element 301.

A correction unit 307 corrects a count value obtained by counting the digital values obtained from the comparison unit 303, that is, the number of the signal levels by using the obtained correction coefficient 308 and holds the corrected count value. In this example, a correction unit 307-H for the high energy region and a correction unit 307-L for the low energy region are included, and the correction coefficients are individually provided to the respective correction units. Subsequently, the corrected count value is output from the output unit 305 as the pixel value of each of the energy regions.

Figure 9B:
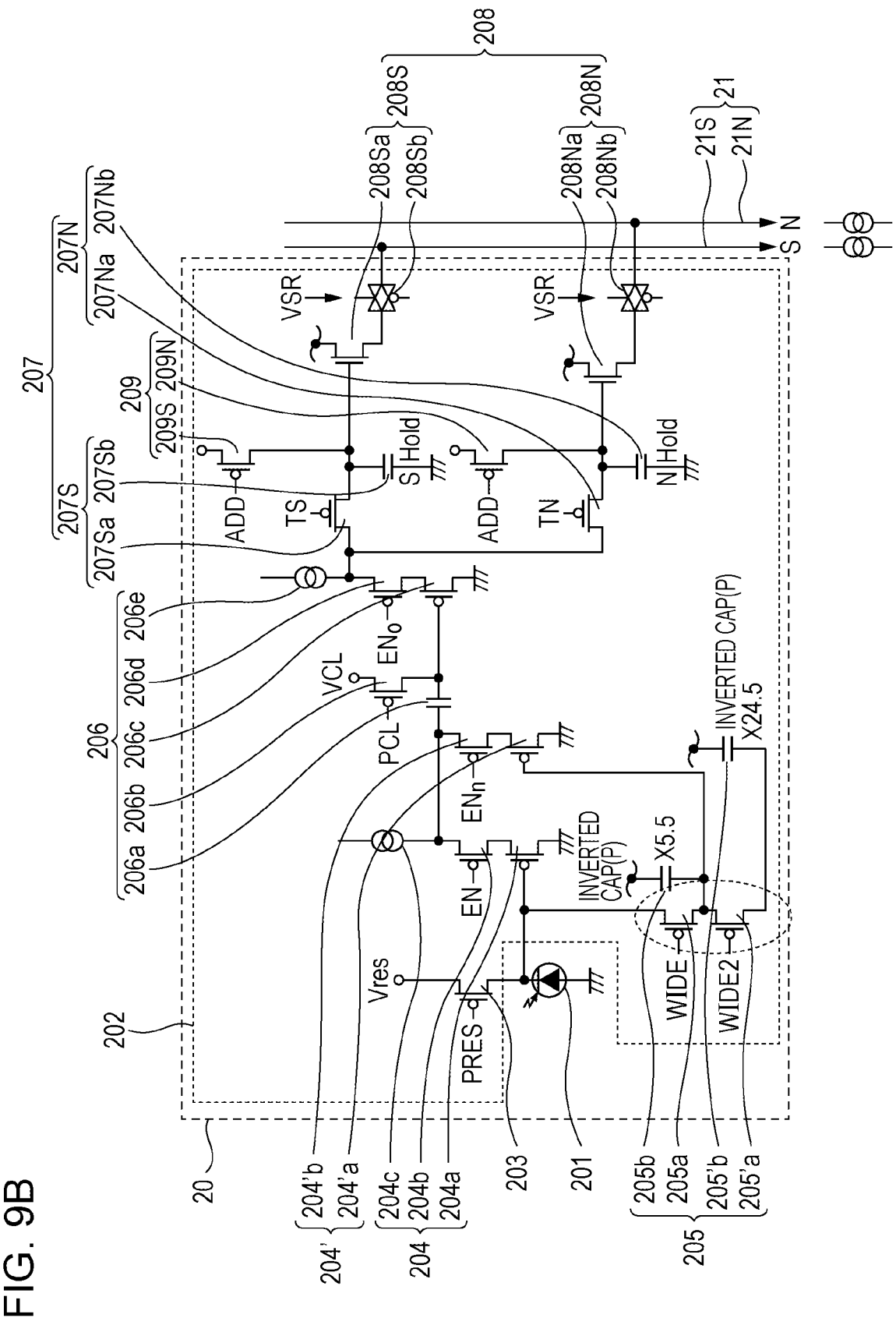
FIG. 9B is a block diagram illustrating a schematic configuration of another example of the pixel.

Next, another example of the pixel 20 of the radiation imaging apparatus that may be applied to the embodiment of the present invention will be described with reference to FIG. 9B. FIG. 9B is a schematic block diagram of a single pixel for describing another example of the pixel 20. The pixel 20 includes the photoelectric conversion element 201 and the pixel circuit unit 202. The pixel circuit unit 202 includes an amplification circuit unit 204, a clamp circuit unit 206, a sample-and-hold circuit unit 207, and a selection circuit unit 208.

The photoelectric conversion element 201 includes a charge accumulation unit, and the charge accumulation unit is connected to a gate of a MOS transistor 204a of the amplification circuit unit 204. A source of the MOS transistor 204a is connected to a current source 204c via a MOS transistor 204b. The MOS transistor 204a and the current source 204c constitute a source follower circuit. The MOS transistor 204b is an enable switch. The MOS transistor 204b is turned on when an enable signal EN supplied to a gate of the MOS transistor 204b turns to an active level and puts the source follower circuit into an operating state.

In the example illustrated in FIGS. 5A and 5B, the charge accumulation unit of the photoelectric conversion element 201 and the gate of the MOS transistor 204a constitute a common node, and this node functions as a charge voltage conversion unit configured to convert charges accumulated in the charge accumulation unit into a voltage. That is, a voltage V (=Q/C) defined by charges Q accumulated in the charge accumulation unit and a capacitance value C of the charge voltage conversion unit appears in the charge voltage conversion unit. The charge voltage conversion unit is connected to a reset potential Vres via a reset switch 203. When a reset signal PRES turns to the active level, the reset switch 203 is turned on, and a potential of the charge voltage conversion unit is reset to the reset potential Vres.

The clamp circuit unit 206 clamps noise output by the amplification circuit unit 204 by a clamp capacitance 206a in accordance with the potential of the reset charge voltage conversion unit. That is, the clamp circuit unit 206 is a circuit configured to cancel this noise from the signal output from the source follower circuit in accordance with the charges generated through the photoelectric conversion by the photoelectric conversion element 201. This noise includes kTC noise at the time of the resetting. Clamping is performed in the following manner. That is, after a clamp signal PCL is set to be at the active level to put a MOS transistor 206b into an ON state, the clamp signal PCL is set to be at an inactive level to put the MOS transistor 206b in an OFF state. An output side of the clamp capacitance 206a is connected to a gate of a MOS transistor 206c. A source of the MOS transistor 206c is connected to a current source 206e via a MOS transistor 206d. The MOS transistor 206c and the current source 206e constitute the source follower circuit. The MOS transistor 206d is an enable switch. The MOS transistor 206d is turned on when an enable signal EN0 supplied to a gate of the MOS transistor 206d turns to the active level and puts the source follower circuit in the operating state.

The signal output from the clamp circuit unit 206 in accordance with the charges generated through the photoelectric conversion by the photoelectric conversion element 201 is written in a capacitance 207Sb via a switch 207Sa as an optical signal when an optical signal sampling signal TS turns to the active level. The signal that is output from the clamp circuit unit 206 when the MOS transistor 206b is put into the ON state immediately after the reset of the potential of the charge voltage conversion unit, is noise. This noise is written in a capacitance 207Nb via a switch 207Na when a noise sampling signal TN turns to the active level. This noise includes an offset component of the clamp circuit unit 206. The switch 207Sa and the capacitance 207Sb constitute a signal sample-and-hold circuit 207S, and the switch 207Na and the capacitance 207Nb constitute a noise sample-and-hold circuit 207N. The sample-and-hold circuit unit 207 includes the signal sample-and-hold circuit 207S and the noise sample-and-hold circuit 207N.

When the driving circuit unit 21 drives a row selection signal VST at the active level, the signal (optical signal) held in the capacitance 207Sb is output to a signal line 25S via a MOS transistor 208Sa and a row selection switch 208Sb. In addition, at the same time, the signal (noise) held in the capacitance 207Nb is output to a signal line 25N via a MOS transistor 208Na and a row selection switch 208Nb. The MOS transistor 208Sa constitutes the source follower circuit together with a constant current source (not illustrated) included in the signal line 25S. Similarly, the MOS transistor 208Na constitutes the source follower circuit together with the constant current source (not illustrated) included in the signal line 25N. The MOS transistor 208Sa and the row selection switch 208Sb constitute the selection circuit unit 208S for the signal, and the MOS transistor 208Na and the row selection switch 208Nb constitute the selection circuit unit 208N for the noise. The selection circuit unit 208 includes the selection circuit unit 208S for the signal and the selection circuit unit 208N for the noise.

The pixel 20 may include an addition switch 209S configured to add optical signals of the plurality of adjacent pixels 20 to each other. At a time in an addition mode, an addition mode signal ADD turns to the active level to put the addition switch 209S into the ON state. Accordingly, the capacitances 207Sb of the adjacent pixels 20 are connected to each other by the addition switch 209S, and the optical signals are averaged. Similarly, the pixel 20 may include an addition switch 209N configured to add noises of the plurality of adjacent pixels 20 to each other. When the addition switch 209N is put into the ON state, the capacitances 207Nb of the adjacent pixels 20 are connected to each other by the addition switch 209N, and the noises are averaged. An addition unit 209 includes the addition switch 209S and the addition switch 209N.

The pixel 20 may include a sensitivity change unit 205 configured to change a sensitivity. The pixel 20 may include, for example, a first sensitivity change switch 205a and a second sensitivity change switch 205'a, and also circuit elements accompanied by those switches. When a first change signal WIDE turns to the active level, the first sensitivity change switch 205a is turned on, and a capacitance value of a first additional capacitance 205b is added to a capacitance value of the charge voltage conversion unit. As a result, the sensitivity of the pixel 20 is decreased. When a second change signal WIDE2 turns to the active level, the second sensitivity change switch 205'a is turned on, and a capacitance value of a second additional capacitance 205'b is added to the capacitance value of the charge voltage conversion unit. As a result, the sensitivity of the pixel 20 is further decreased. In this manner, while the function of decreasing the sensitivity of the pixel 20 is added, the still larger light quantity can be received, and it is possible to expand a dynamic range. In a case where the first change signal WIDE turns to the active level, while an enable signal ENw is set to be at the active level, a MOS transistor 204'a may be caused to perform the source follower operation in addition to the MOS transistor 204a.

According to the above-described configuration, the signal processing unit 105 or the control computer 13 may perform processing for energy discrimination. For example, a pixel value is readout at a high speed such that the pixel value is equivalent to a signal of one photon, and this pixel value is counted by the signal processing unit 105 or the control computer 13. With this configuration, it is possible to obtain the energy-discriminated radiographic image by counting the number of photons. In addition, while a variance and an average are statistically obtained on the basis of a pixel value obtained from an arbitrary pixel to estimate the number of photons and an average value of energy of radiation quanta in the arbitrary pixel, it is possible to obtain the energy-discriminated radiographic image.

It should be noted that the above-described processing is preferably executed by using a program, but all or part of the processing may be executed by using a circuit. In addition, the processing may be executed by at least one of the signal processing unit 105 and the control computer 13 or may be executed by utilizing both the signal processing unit 105 and the control computer 13. That is, the signal processing unit or the signal processing apparatus for the radiographic image according to the embodiment of the present invention is equivalent to at least one of the signal processing unit 105, the control computer 13, and the signal processing unit 105 and the control computer 13.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

REFERENCE SIGNS LIST

20 Pixel
101 Detector
102 Pixel array
105 Signal processing unit
108 Conversion unit

The invention claimed is:

1. A radiation imaging system comprising:
a detector including a conversion unit configured to convert incident radiation photons into optical photons or charges, a pixel array including pixels arranged in a two-dimensional matrix and configured to obtain a pixel value in accordance with the optical photons or charges, and an output circuit including a plurality of output channels configured to output the pixel value from the pixel array; and
a signal processing unit configured to perform signal processing of correcting the pixel value by using a correction coefficient in accordance with a pixel value obtaining process model in which a process of obtaining the pixel value output from the pixel array via the plurality of output channels on the basis of the optical photons or charges is modeled and obtaining an energy-discriminated radiographic image based on the corrected pixel value,
wherein the output circuit has individual circuits for each of the plurality of output channels of the pixel array, and each of the individual circuits has its own intrinsic noise, and
wherein the correction coefficient is calculated further on the basis of a fixed pattern noise that may be added to each of the pixel values outputted from the pixel array, the fixed pattern noise comprising the intrinsic noise.

2. The radiation imaging system according to claim 1, wherein the correction coefficient is prepared further in accordance with a photon conversion process model in which a process of converting the radiation photons into the optical photons or charges is modeled.

3. The radiation imaging system according to claim 2, wherein the correction coefficient is calculated on the basis of secondary radiation that may be generated during the process of converting the radiation photons into the optical photons or charges, diffusion of the optical photons or charges, and noise that causes an output variation in the semiconductor element.

4. The radiation imaging system according to claim 3,
wherein the conversion unit may generate the secondary radiation in a case where energy of the radiation photons is higher than or equal to excitation energy, and
wherein the photon conversion process model is modeled by using the excitation energy and a generation ratio of the optical photons or charges corresponding to energy of the radiation photons as parameters.

5. The radiation imaging system according to claim 4,
wherein, in a histogram of an output level of the pixel array in which a horizontal axis represents a signal level output from the pixel array and a vertical axis represents the number of the signal levels, the pixel value obtaining process model is modeled by using a shape of the histogram and a size of the histogram as parameters.

6. The radiation imaging system according to claim 5, wherein the pixel value obtaining process model is modeled by deriving the shape of the histogram and the size of the histogram on the basis of the histogram prepared on the basis of a signal output from a radiation imaging apparatus irradiated with radiation having energy lower than the excitation energy.

7. The radiation imaging system according to claim 6, wherein the photon conversion process model is modeled by deriving the generation ratio by performing fitting of the histogram prepared on the basis of the signal output from the radiation imaging apparatus irradiated with the radiation having the energy lower than the excitation energy and a virtual histogram generated by using the excitation energy, the shape of the histogram, and the size of the histogram while the generation ratio is used as a variable value.

8. The radiation imaging system according to claim 7, wherein the correction coefficient is derived on the basis of an output simulation result of the radiation imaging apparatus obtained by applying the photon conversion process model and the pixel value obtaining process model to information related to emitted radiation.

9. The radiation imaging system according to claim 5, wherein the conversion unit includes a scintillator configured to convert the radiation photons into the optical photons.

10. The radiation imaging system according to claim 9, wherein each of the plurality of pixels includes a photoelectric conversion unit configured to convert the optical photons into a signal, a comparison unit configured to compare the signal with a reference voltage to output a digital value, a correction unit configured to correct the digital value output from the comparison unit by using the correction coefficient and hold the digital value, and an output unit configured to output a pixel value in accordance with the digital value output from the correction unit.

11. A signal processing apparatus configured to perform signal processing of performing correction by using a pixel value obtained in accordance with optical photons or charges converted from radiation photons incident on a detector including a conversion unit configured to convert incident radiation photons into optical photons or charges, a pixel array including pixels arranged in a two-dimensional matrix and configured to obtain a pixel value in accordance with the optical photons or charges, and an output circuit including a plurality of output channels configured to output the pixel value from the pixel array and obtaining an energy-discriminated radiographic image obtained on the basis of the corrected pixel value, by using a correction coefficient in accordance with a pixel value obtaining process model in which a process of obtaining the pixel value output from the pixel array via the plurality of output channels on the basis of the optical photons or charges is modeled,
wherein the output circuit has individual circuits for each of the plurality of output channels of the pixel array, and each of the individual circuits has its own intrinsic noise, and
wherein the correction coefficient is calculated further on the basis of a fixed pattern noise that may be added to each of the pixel values outputted from the pixel array, the fixed pattern noise comprising the intrinsic noise.

12. A signal processing method comprising:
performing signal processing of performing correction by using a pixel value obtained in accordance with optical photons or charges converted from radiation photons incident on a detector including a conversion unit configured to convert incident radiation photons into optical photons or charges, a pixel array including pixels arranged in a two-dimensional matrix and configured to obtain a pixel value in accordance with the optical photons or charges, and an output circuit including a plurality of output channels configured to output the pixel value from the pixel array and obtaining an energy-discriminated radiographic image obtained on the basis of the corrected pixel value, by using a correction coefficient in accordance with a pixel value obtaining process model in which a process of obtaining the pixel value output from the pixel array via the plurality of output channels on the basis of the optical photons or charges is modeled, wherein the output circuit has individual circuits for each of the plurality of output channels of the pixel array, and each of the individual circuits has its own intrinsic noise, and wherein the correction coefficient is calculated further on the basis of a fixed pattern noise that may be added to each of the pixel values outputted from the pixel array, the fixed pattern noise comprising the intrinsic noise.

* * * * *